US009833226B2

(12) United States Patent
Engh et al.

(10) Patent No.: US 9,833,226 B2
(45) Date of Patent: Dec. 5, 2017

(54) ENDOSCOPIC PORTS FOR MINIMALLY INVASIVE SURGICAL ACCESS AND METHODS OF USE THEREOF

(71) Applicant: University of Pittsburgh—Of the Commonwealth System of Higher Education, Pittsburgh, PA (US)

(72) Inventors: Johnathan Engh, Pittsburgh, PA (US); Gregg Podnar, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 15/181,259

(22) Filed: Jun. 13, 2016

(65) Prior Publication Data

US 2016/0287239 A1     Oct. 6, 2016

Related U.S. Application Data

(62) Division of application No. 13/878,169, filed as application No. PCT/US2011/054957 on Oct. 5, 2011, now Pat. No. 9,386,972.

(60) Provisional application No. 61/389,928, filed on Oct. 5, 2010.

(51) Int. Cl.
| | |
|---|---|
| *A61B 1/32* | (2006.01) |
| *A61B 17/02* | (2006.01) |
| *A61B 1/313* | (2006.01) |
| *A61B 17/34* | (2006.01) |
| *A61B 17/00* | (2006.01) |

(52) U.S. Cl.
CPC ........ *A61B 17/0218* (2013.01); *A61B 1/3135* (2013.01); *A61B 1/32* (2013.01); *A61B 17/3439* (2013.01); *A61B 17/3421* (2013.01); *A61B 2017/00557* (2013.01)

(58) Field of Classification Search
CPC ..... A61B 17/0218; A61B 1/3135; A61B 1/32; A61B 17/3421; A61B 17/3439; A61B 2017/00557
USPC .... 600/184–199, 201–210; 606/190–194, 99
See application file for complete search history.

(56) References Cited

U.S. PATENT DOCUMENTS

| | | | |
|---|---|---|---|
| 3,253,594 A | 5/1966 | Matthews et al. | |
| 5,562,696 A * | 10/1996 | Nobles ................. | A61B 1/042 600/101 |
| 5,620,456 A * | 4/1997 | Sauer ................. | A61B 17/3417 604/164.01 |

(Continued)

OTHER PUBLICATIONS

International Search Report and Written Opinion for international application No. PCT/US2011/054957, dated May 16, 2012 by the Korean Intellectual Property Office acting as the International Searching Authority (8 pages).

*Primary Examiner* — Eduardo C Robert
*Assistant Examiner* — Tara R Carter
(74) *Attorney, Agent, or Firm* — Klarquist Sparkman, LLP

(57) ABSTRACT

A method for providing an endoscopic port includes inserting a distal portion of an expandable member into soft tissue in a patient's body. The distal portion of the expandable member is inflated to form a passageway in the soft tissue. A rigid tube member is delivered into the passageway formed by the expandable member through the inside of the inflatable member. A port is established between a proximal opening in the rigid tube member and a distal opening in the rigid tube member.

11 Claims, 5 Drawing Sheets

(56) References Cited

U.S. PATENT DOCUMENTS

| | | | |
|---|---|---|---|
| 6,319,191 B1 | 11/2001 | Sayet et al. | |
| 7,344,547 B2 * | 3/2008 | Piskun | A61B 17/0218 606/185 |
| 7,398,781 B1 | 7/2008 | Chin | |
| 7,527,636 B2 | 5/2009 | Dunfee et al. | |
| 2008/0086167 A1 | 4/2008 | Mastri et al. | |
| 2009/0048622 A1 | 2/2009 | Wilson | |
| 2009/0216284 A1 | 8/2009 | Chin | |
| 2010/0048990 A1 | 2/2010 | Bakos | |
| 2010/0198005 A1 | 8/2010 | Fox | |
| 2010/0312066 A1 * | 12/2010 | Cropper | A61B 17/3423 600/207 |
| 2011/0144590 A1 | 6/2011 | Sakai et al. | |

* cited by examiner

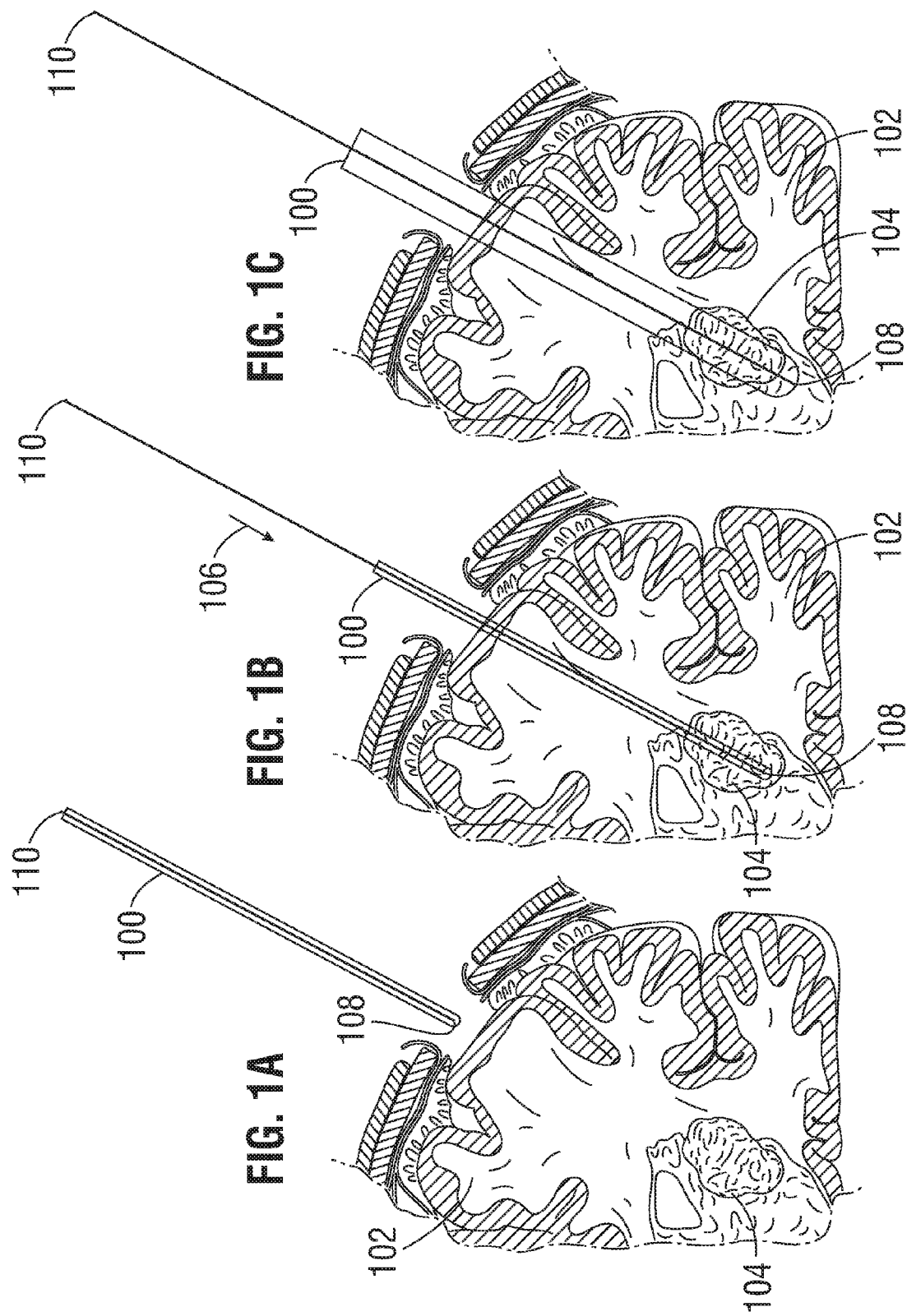

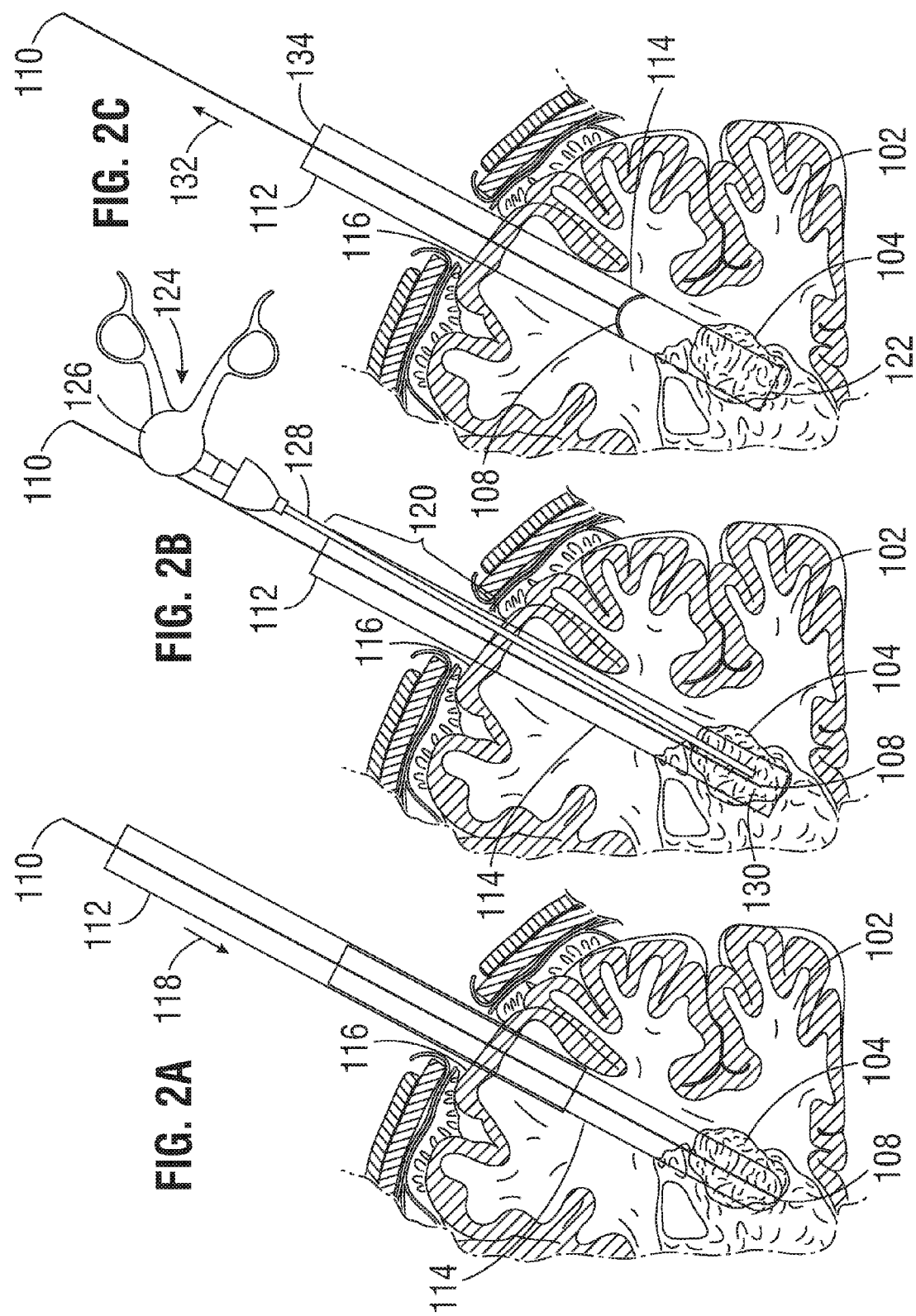

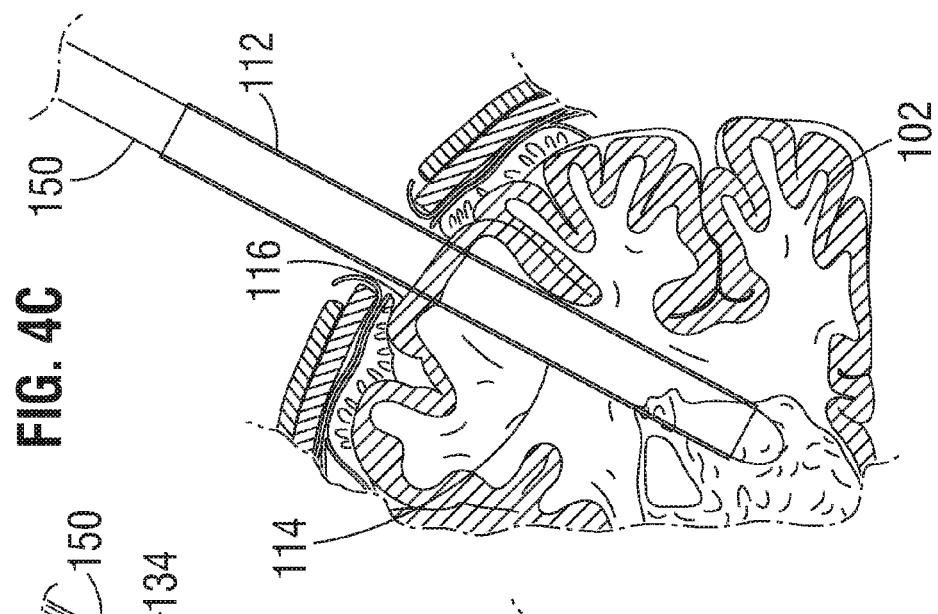
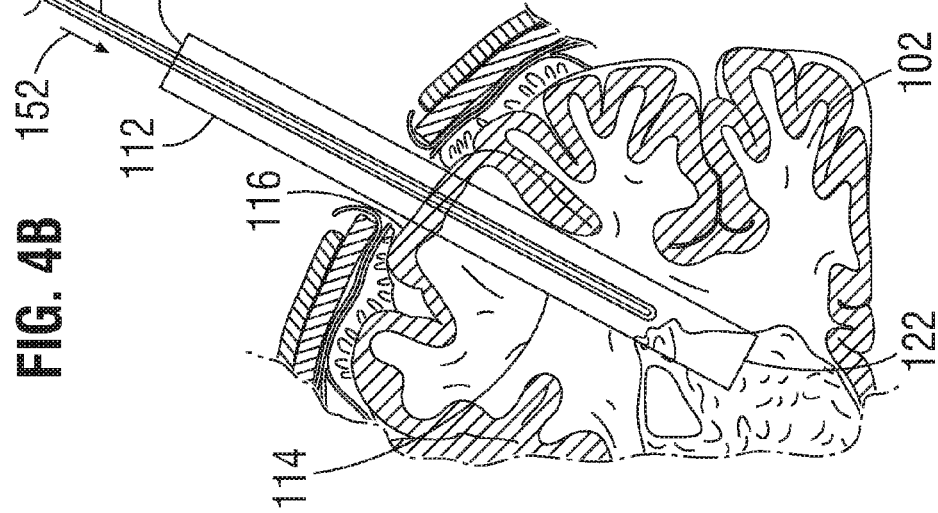
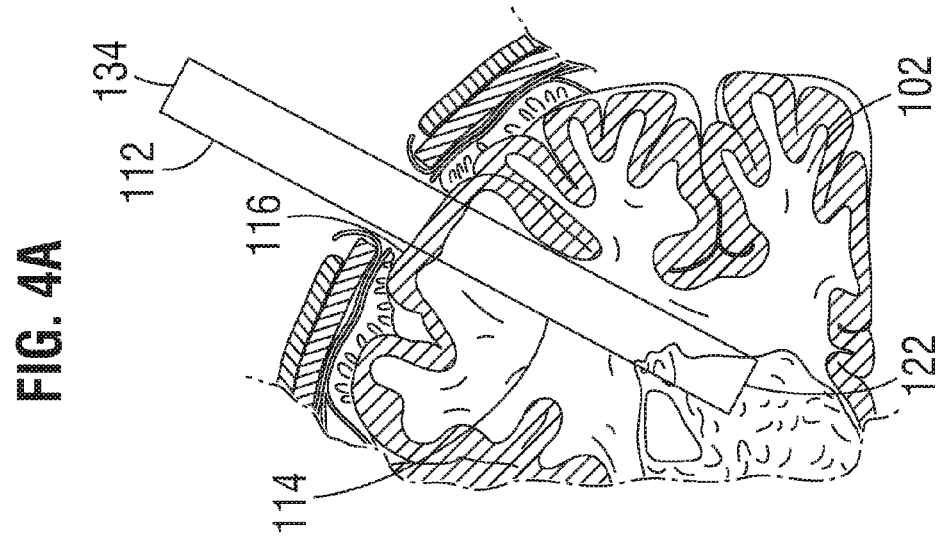

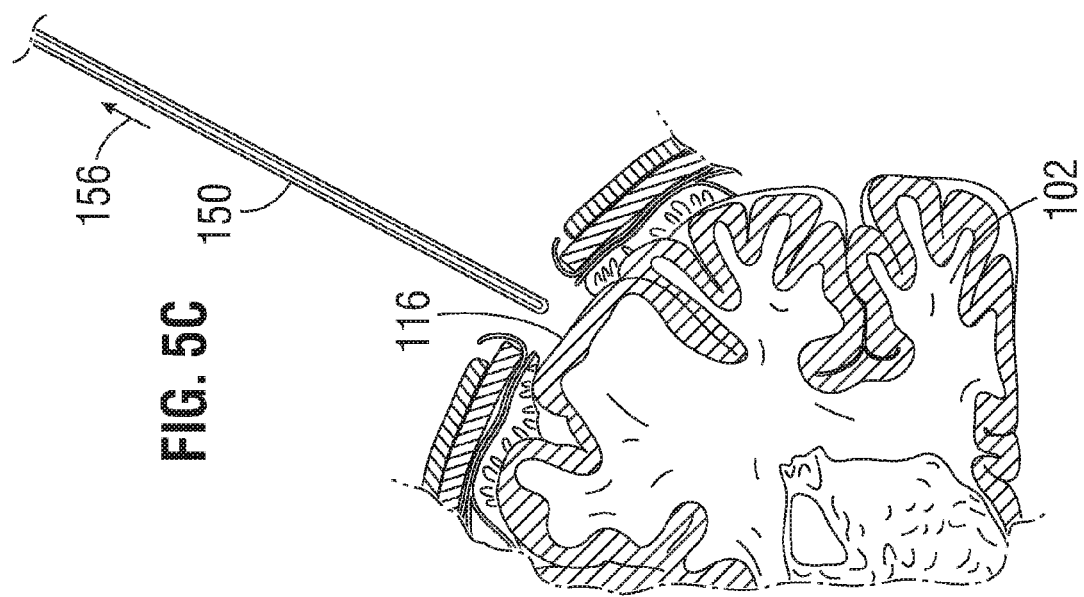
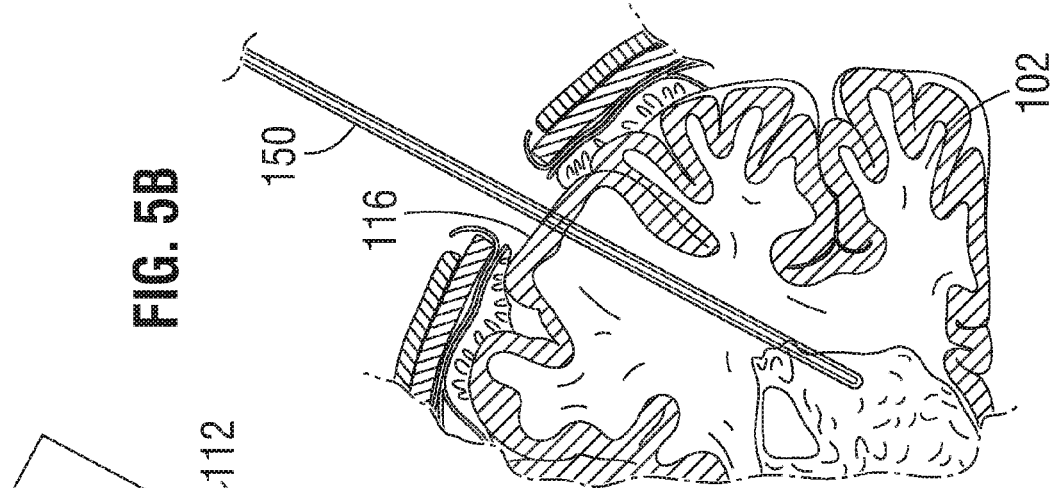
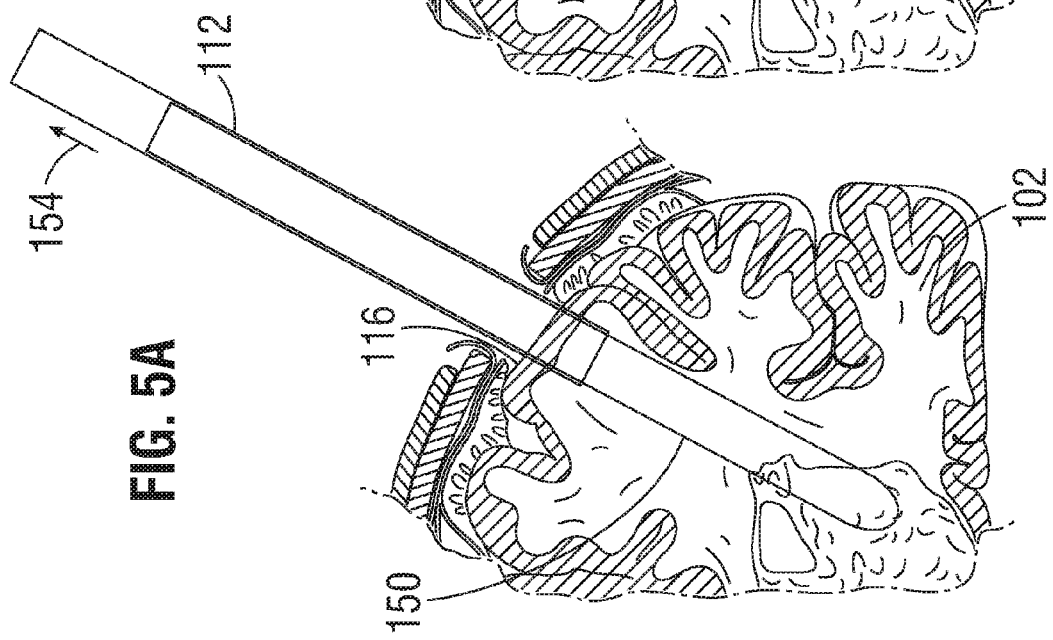

ENDOSCOPIC PORTS FOR MINIMALLY INVASIVE SURGICAL ACCESS AND METHODS OF USE THEREOF

CROSS REFERENCE TO RELATED APPLICATIONS

This is a divisional of U.S. application Ser. No. 13/878,169, filed Apr. 5, 2013, which is the U.S. National Stage of International Application No. PCT/US2011/054957, filed Oct. 5, 2011, which was published in English under PCT Article 21(2), which in turn claims the benefit of priority of U.S. Provisional Application No. 61/389,928, filed Oct. 5, 2010; each of these applications is specifically incorporated by reference herein in its entirety.

FIELD

The present disclosure relates to endoscopic ports and method for using the same in connection with various surgical procedures.

BACKGROUND

Various conditions, illness, and/or injuries that affect the brain require surgical procedures to provide access to the brain in order to treat the affected area. For example, many brain tumors are life-threatening and require a surgical procedure to access and remove at least a portion of the tumor. For primary brain tumors, an attempt at maximal surgical resection is often the preferred treatment, usually followed by adjuvant chemotherapy and radiation therapy. For brain metastases, resection is often recommended for large, symptomatic metastases as well as for single metastases in patients with otherwise high functional status. Appropriate tumor removal facilitates neurologic recovery, functional recovery, and sometimes survival.

However, safely providing access to such treatment areas can be challenging. For example, the vast majority of intraparenchymal brain tumors are surrounded by a "cuff" of overlying brain cortex as well as subcortical white matter, which in turn, surrounds the actual tumor. Much of the morbidity and risk inherent to brain tumor surgery is related to the manipulation and dissection of this tissue. In addition, the amount of dissection of overlying brain increases with increasing lesional depth. As a result, the risk of neurological injury and surgical complications can be even greater for deep-seated brain tumors.

SUMMARY

In a first embodiment, an endoscopic port apparatus is provided. The apparatus includes an inflatable member, a rigid tube member, a housing, and an actuator. The inflatable member has a proximal portion and a distal portion. At least the distal portion of the inflatable tube member is inflatable between a collapsed state and an expanded state. The housing has an interior space configured to receive the rigid tube member. The actuator is configured to exert a force on the rigid tube member to cause it to move from the interior space in the housing into the distal portion of the inflatable member when the inflatable member is in the expanded state.

In some embodiments, a guide member extends into the inflatable member to increase the rigidity of the inflatable member. The guide member can be coupled to a distal end of the inflatable member to facilitate removal of the distal end of the inflatable member to establish a distal opening in the rigid tube member. In other embodiments, the actuator comprises a plunger, a motorized linear actuator, and/or a magnetic member that is coupled to the rigid tube to exert a force on the rigid tube member to push the rigid tube member into the distal portion of the inflatable member. The rigid tube member can be substantially transparent to improve visibility in the vicinity of the endoscopic port apparatus. In some embodiments, the transparent tube is clear.

In some embodiments, the housing and proximal portion of the inflatable member are maintained in a substantially airtight manner. The proximal portion of the inflatable member can extend into the housing. For example, when the rigid tube member is received in the housing, the rigid tube member is received at least partly within the proximal portion of the inflatable member. In other embodiments, the proximal portion of the inflatable member is coupled to a distal end of the housing, such that when the rigid tube member is received in the housing the rigid tube member does not substantially overlap with the inflatable member.

In another embodiment, a method for providing an endoscopic port is provided. The method includes inserting a distal portion of an expandable member into soft tissue in a patient's body and inflating the distal portion of the expandable member to form a passageway in the soft tissue. A rigid tube member is delivered into the passageway formed by the expandable member. The rigid tube member is delivered inside the inflated distal portion of the inflatable member and a port is established between a proximal opening in the rigid tube member and a distal opening in the rigid tube member.

In some embodiments, establishing the port comprises cutting a distal end of the expandable member and removing the cut distal end from within the rigid tube member. In other embodiments, the insertion of the distal portion of the expandable member comprises inserting a guide member into the distal portion and directing the guide member and distal portion of the expandable member through the soft tissue. The guide member can be coupled to the distal end of the expandable member and the removal of the cut distal end can include removing the guide member from within the rigid tube member. In other embodiments, establishing the port further comprises cutting the expandable member around the proximal opening of the rigid tube member.

In some embodiments, the rigid tube member can be positioned within a housing and the rigid tube member can be delivered into the passageway by exerting a force on the rigid tube member to push it into the inflated distal portion of the inflatable member. In other embodiments, a proximal portion of the inflatable member can extend into the housing and the rigid tube member is positioned inside the proximal portion of the inflation member before being delivered into the passageway. The exertion of the force on the rigid tube member to push it into the inflated distal portion of the inflatable member can be achieved by manually depressing a plunger, activating a motorized linear actuator, and/or magnetically coupling the rigid tube member with an external magnet.

In some embodiments, the method further comprises inserting a second expandable member into the rigid tube member, at least partially inflating the second expandable member within the endoscopic port, removing the rigid tube member from the passageway, and deflating the expandable member to reduce the speed at which the soft tissue surrounding the passageway expands to fill the passageway upon removal of the rigid tube member.

In another embodiment, a method for providing an endoscopic port includes inserting a distal portion of an expandable member into soft tissue in a patient's body, inflating the distal portion of the expandable member to form a passageway in the soft tissue, delivering a rigid tube member into the passageway formed by the expandable member, and removing the expandable member to establish a port between a proximal opening in the rigid tube member and a distal opening in the rigid tube member. The rigid tube member is delivered along an outside surface of the inflated distal portion of the inflatable member.

In yet another embodiment, a method for removing an endoscopic port includes inserting an expandable member into a passageway formed by an endoscopic port, at least partially inflating the second expandable member within the endoscopic port, removing the rigid tube member from the passageway, and deflating the expandable member to reduce the speed at which the soft tissue surrounding the passageway expands to fill the passageway upon removal of the rigid tube member.

The foregoing and other objects, features, and advantages of the invention will become more apparent from the following detailed description, which proceeds with reference to the accompanying figures.

BRIEF DESCRIPTION OF THE DRAWINGS

FIGS. 1A-1C illustrate an embodiment in which an expandable member is delivered into soft tissue of a patient and expanded to form a passageway.

FIGS. 2A-2C illustrate an embodiment in which an endoscopic port is formed by inserting a rigid tube into a passageway in a patient.

FIGS. 4A-4C illustrate an embodiment for reducing trauma to a patient during removal of an endoscopic port.

FIGS. 5A-5C illustrate additional steps in the embodiment shown in FIGS. 4A-4C.

DETAILED DESCRIPTION

Figures 3A, 3B, 3C, 3D, 3E, 3F, 3G, 3H:
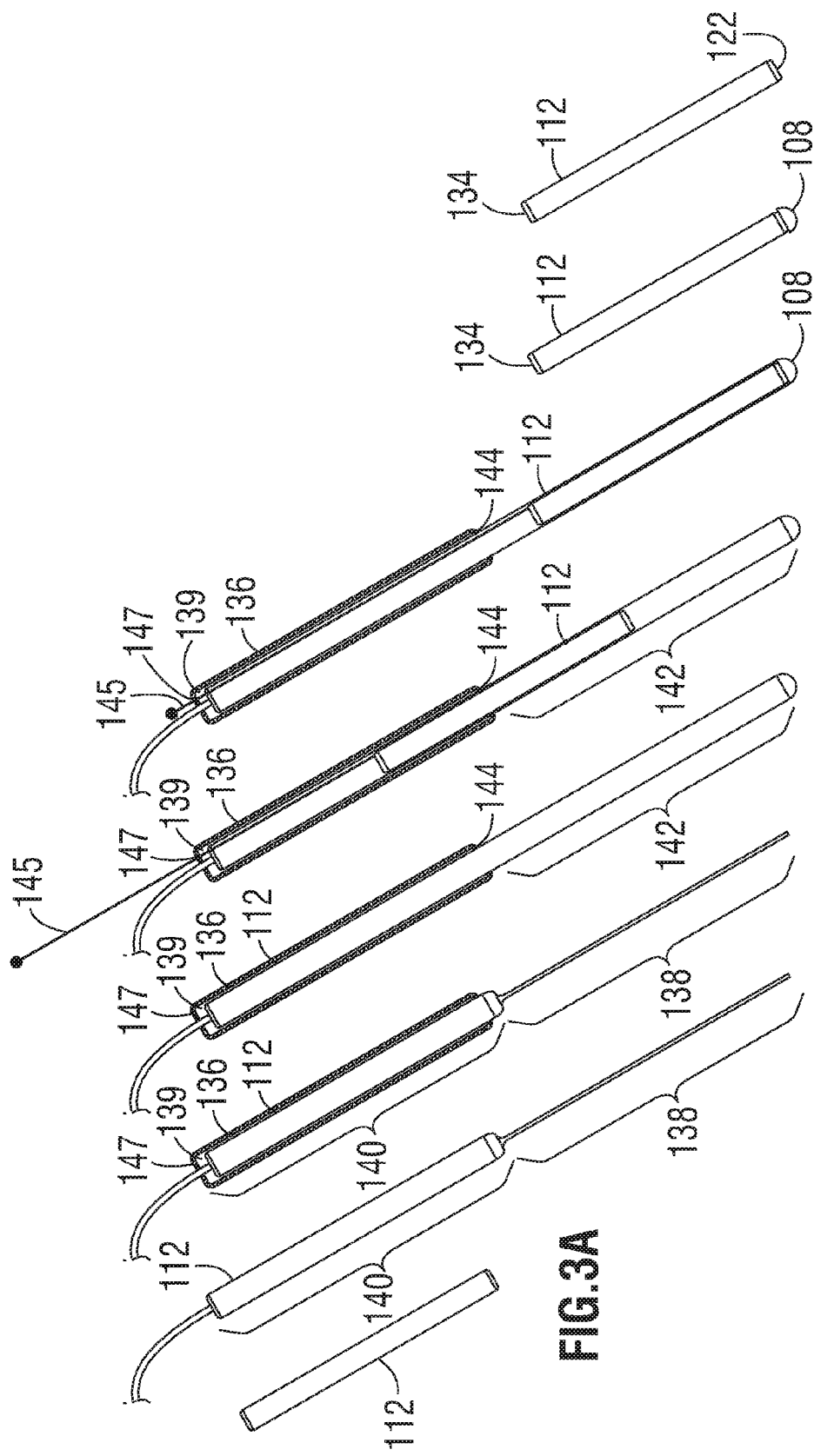
FIGS. 3A-3H illustrate an embodiment in which an endoscopic port is formed by inserting a rigid tube into a passageway in a patient.

Various embodiments of endoscopic port technology and their methods of use are disclosed herein. The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently.

Further, descriptions and disclosures provided in association with one particular embodiment are not limited to that embodiment, and may be applied to any embodiment disclosed.

FIGS. 1A-1C illustrate an embodiment of an endoscopic port apparatus and a method of using the same. FIG. 1A illustrates an inflatable member 100 that is inflatable from a collapsed state (FIG. 1A) to an expanded state (FIG. 1C). As shown in FIG. 1B, when inflatable member 100 is in the collapsed state, it has a relatively low profile that permits a distal end 108 of inflatable member 100 to be maneuvered through a portion of the brain 102 (or other soft tissue of the patient) until it reaches to a location of interest. Thus, for example, distal end 108 of inflatable member 100 can be delivered through the cortex and white matter of the brain 102 in a direction that is indicated by arrow 106 (FIG. 1B). Once distal end 108 of inflation member 100 reaches the desired location (e.g., at or adjacent to the location of a lesion 104), inflation member 100 can be inflated to the expanded state as shown in FIG. 1C. The delivery of inflation member 100 to the desired location in the body can be facilitated by various imaging techniques such as magnetic resonance imaging (MRI) and/or non-imaging techniques such as frame-based or frameless stereotactic guiding systems.

Inflatable member 100 can comprise a tubular balloon catheter made of non-compliant or semi-compliant material. In some embodiments, inflatable member 100, or portions thereof, can be substantially transparent allowing for visualization through inflatable member 100. The term "transparent" as used herein refers to the ability see through the tube member or other transparent structure. Transparent elements, therefore, include "clear" elements, which provide substantially unimpeded views through the element.

When inflated, inflatable member 100 forms a longitudinally extending lumen that is large enough to permit passage of other instruments, as described below. The material of the expandable portion of inflation member 100 is desirably selected so that it has sufficient structural integrity to achieve inflation pressures suitable for dilating the brain tissue in the manners disclosed herein. To provide additional rigidity to inflatable member 100 and/or to facilitate the maneuvering of inflatable member to the desired location, a guide member 110 can extend through inflation member 100 as shown in FIGS. 1A-1C.

In some embodiments, guide member 110 can extend through inflation member 100 so that a distal end of guide member 110 is adjacent distal end 108 while distal end 108 is being delivered into the body of the patient. Also, if desired, a proximal end (not shown) of guide member can extend beyond the proximal end of inflation member 100 for manipulation by the surgeon to facilitate delivery of the distal end 108 of inflation member 100 to the desired location of interest within the body of the patient.

After distal end 108 of inflation member 100 is delivered to the desired location, an inflation device (not shown) with one or more ports in fluid connection with a fluid source (not shown) can deliver an expansion fluid (e.g., air, saline, etc.) into inflation member 100 to cause inflation member 100 to expand from the collapsed state to the expanded state. Inflation of inflatable member 100 can be performed slowly to cause the surrounding brain tissue to retract in a substantially atraumatic manner. As inflation member 100 expands, the portion of expansion member 100 within the body forms a passageway 114 (FIG. 2A) within the body. Passageway 114 extends from an exterior surface or area of the patient (e.g., an exterior brain surface 116) to the distal end 108 of inflation device 100.

To maintain the opening into the body provided by passageway 114 and provide a surgeon with access to the internal area of the patient in the vicinity of the distal end 108 of inflation member 100 (e.g., lesion 104), a rigid tube member 112 can be delivered through the lumen of the expanded inflation member 100 and into passageway 114. Rigid tube member 112 is desirably a generally transparent tube that allows the surgeon to visualize the anatomy surrounding rigid tube member 112.

FIGS. 2A-2C illustrate the delivery of rigid tube member 112 from a first position that is outside of the body of the patient to a second position that is at least partially within the body of the patient to establish a port between openings at the two opposing ends of rigid tube member 112. In the first position, rigid tube member 112 is positioned within inflatable member 100 at a location external to the body of the patient. Rigid tube member 112 can be pre-loaded or pre-installed in the proximal portion of inflatable member 100 before the inflatable member 100 member is introduced into the patient (see, e.g., FIG. 3B). After inflatable member 100 is expanded (e.g., FIG. 1C), rigid tube member 112 is moved in the direction of arrow 118 into passageway 114 as shown in FIG. 2A.

FIG. 2A illustrates rigid tube member 112 partially delivered to a desired location within the body and FIG. 2B illustrates rigid tube member 112 fully delivered to a desired location within the body. In some embodiments, when rigid tube member 112 is fully delivered (e.g., FIG. 2B), rigid tube member 112 extends substantially through passageway 114. A portion of rigid tube member 112 (e.g., proximal portion 120) can extend beyond passageway 114 and out of the body of the patient.

After rigid tube member 112 is fully delivered, the fluid pressure inside inflatable member 100 can be reduced. As the fluid pressure in the tubular balloon is reduced, inflatable member 100 is at least partially collapsed so that an inside diameter of inflation member 100 is reduced. When the portion of inflation member 100 that surrounds rigid tube member 112 reduces in diameter a sufficient amount, an inside surface of inflation member 100 will contact an outside surface of rigid tube member 112 and effectively form a double-walled rigid tube. The material of the expandable portion of the inflation member 100 can be selected so that the material exhibits an amount of elasticity (e.g., stretch) that is adequate to provide a sufficient amount of frictional adhesion between the inside surface of the tubular balloon and the outside surface of rigid tube member 112 to effectively form a single piece double-walled tube when the fluid pressure within inflation member 100 is released.

Once rigid tube member 112 is in the desired position and the fluid pressure within inflation member 100 is released to form a double-walled tube, a port can be established between the two openings of rigid tube member 112 by removing portions of inflatable member 100. For example, the distal end 108 of inflatable member 100 can be removed to provide access to a distal opening 122 of rigid tube member 112.

The distal end 108 of inflatable member 100 can be separated at the distal opening 122 of the rigid tube via sharp dissection and the separated distal end 108 can be removed from the rigid tube. For example, as shown in FIG. 2B, the distal end 108 of inflatable member 100 can be cut using a tool, such as a pair of rotatable scissors 124 with an external handle member 126. The cutting portion 130 of the rotatable scissors 124 can be positioned at the end of a shaft 128 that is long enough to extend through rigid tube member 112 to reach the distal end 108 of inflatable member 100. As shown in FIG. 2C, after distal end 108 is cut by the cutting portion 130 of rotatable scissors 124, the cut distal end 108 can be removed through the inside of rigid tube member 112. Cut distal end 108 can be removed by any means sufficient to capture and pull the cut distal end 108 out of rigid tube member 112 in the direction indicated by arrow 132.

In one embodiment, guide member 110 can be coupled to the distal end 108 of inflatable member 100 such that after the distal end 108 is cut, the cut distal end 108 can be removed by simply pulling guide member 110 out of rigid tube member 112. Accordingly, in this embodiment, guide member 110 can facilitate delivery of the distal end 108 to the desired location and facilitate removal of the distal end 108 after the rigid tube member 112 is positioned within passageway 114.

After removal of the distal end 108 lesion 104 is generally accessible through the distal opening 122 of rigid tube member 112. If desired, inflatable member 100 can also be cut in the area of a proximal opening 134 of rigid tube member 112 (see, e.g., FIG. 2C) to provide access through rigid tube member 112 at the proximal opening 134. Cutting or removing inflatable member 100 in the area of the proximal opening 134 can be performed in various ways. If a proximal end of the rigid tube member 112 extends out of the body as shown in FIG. 2C, the area of inflatable member 100 around the proximal opening 134 can be easily accessed for cutting, separating, and/or removing the portion of inflatable member 100 that extends proximally from proximal opening 134 in rigid tube member 112. After removal of the distal end 108 and a proximal portion of inflatable member 100, the double-walled endoscopic port formed by rigid tube member 112 and the portion of inflatable member surrounding rigid tube member 112 establishes access into the body through the proximal and distal openings 134, 122.

In other embodiments, a portion of rigid tube member 112 can be removed along with a portion of the proximal end of inflatable member 100. In this manner, the inflatable member 100 and rigid tube member 112 can be cut at any length outside of the body and the distance that rigid tube member 112 extends outside the body can be adjusted by the surgeon in accordance with the surgeon's preferences.

Alternatively, access to the proximal opening 134 can be provided through a proximal end of the inflatable member 100 (not shown). Thus, the rigid tube member 112 can provide a double-walled endoscopic port through which lesion 104 is exposed for resection or other treatment. If desired, one or more clamping or locating mechanisms can be attached to rigid tube member 112 in the vicinity of the proximal opening 134 to secure the rigid tube member 112 in a desired orientation.

Various mechanisms can be used for introducing the rigid tube member 112 into the passageway 114 defined by the expanded inflatable member 100. Referring to FIGS. 3A-3H, a step-by-step process for introducing a rigid tube member 112 using a housing 136 is described.

FIG. 3A illustrates rigid tube member 112. FIG. 3B illustrates rigid tube member 112 pre-installed within inflatable member 100 in its non-inflated, collapsed state, thereby providing a reduced diameter collapsed portion 138 of inflatable member 100 and an enlarged diameter portion 140 that contains rigid tube member 112. When the collapsed portion 138 is expanded, the enlarged diameter portion 140 can also be at least partially inflated since it is in fluid communication with the collapsed portion 138.

FIG. 3C illustrates housing 136, which is configured to be held by the surgeon to facilitate insertion of collapsed portion 138 of inflatable member 100 into the body of the patient (e.g., into the soft tissue of the brain as shown in FIG. 1B). Housing 136 can comprise a handle with an interior area or space 139 for receiving the enlarged diameter portion 140 and rigid tube member 112.

The enlarged diameter portion 140 can have a larger diameter than the collapsed portion 138 in the absence of any expansion forces. In the embodiment illustrated in FIG. 3B, the enlarged diameter portion 140 of inflatable member 100 is constructed so that its inner diameter is slightly larger than the outer diameter of rigid tube member 112. Thus, inflatable member 100, in its collapsed state, has a diameter that varies along its length, with the portion that is contained within the housing 136 having a larger diameter than the portion outside of the housing 136. As shown in FIG. 3C, enlarged diameter portion 140 can substantially fill a cavity (e.g., interior space 139) inside housing 136 and rigid tube member 112 can be positioned inside of the enlarged diameter portion 140 of inflatable member 100. Also, if desired, inflatable member 100 and housing 136 can be coupled together so that movement of housing 136 by the surgeon causes relative movement in the collapsed portion 138 of inflatable member 100.

In an alternative embodiment, the enlarged diameter portion 140 can be expanded (stretched) to its enlarged diameter by the force exerted on it by an outer surface of rigid tube member 112 when rigid tube member 112 is inserted into the enlarged diameter portion 140. To position rigid tube member 112 inside the enlarged diameter portion 140, inflatable member 100 can be fully inflated and rigid tube member 112 can be moved inside the inflated, enlarged diameter portion 140. When the pressure inside inflatable member 100 is released, the enlarged diameter portion 140 can collapse until an internal surface of the enlarged diameter portion 140 fits tightly against the external surface of rigid tube member 112. Thus, the rigid tube member 112 can be positioned inside the enlarged diameter portion 140 so that the enlarged diameter portion 140 is in a stretched, but not inflated, state after it receives rigid tube member 112.

Collapsed portion 138 is desirably formed with a plurality of longitudinal folds to achieve a small diameter profile that is capable of expanding to the desired expansion diameter. During inflation, the plurality of longitudinal folds of the collapsed portion 138 unfold until the partially inflated collapsed portion 138 reaches its net inner diameter. In some embodiments, the net inner diameter is slightly less than the outer diameter of rigid tube member 112. The partially inflated collapsed portion 138 can then be further inflated until reaches a pressure that stretches the collapsed portion 138 to an inner diameter that is slightly larger than the outer diameter of rigid tube member 112.

FIG. 3D illustrates inflatable member 100 in an inflated state. In the inflated state, the collapsed portion 138 shown in FIG. 3C has been inflated to provide an expanded portion 142 that defines a passageway in the body of the patient (e.g., FIG. 1C). FIGS. 3E and 3F illustrate rigid tube member 112 being moved downward (e.g., distally with reference to a patient) into the expanded portion 142 to establish a port in a passageway defined by the expanded portion 142. After rigid tube member 112 is delivered to the desired location within the expanded portion 142, the fluid pressure in inflatable member 100 can be reduced, allowing the expanded portion 142 to be reduced until an inside surface of the inflatable member 100 contacts the outside surface of rigid tube member 112 as described elsewhere herein.

Referring now to FIGS. 3G and 3H, after rigid tube member 112 is in the desired position, the proximal opening 134 and distal opening 122 of rigid tube member 112 can be exposed by cutting, separating, and/or removing portions of inflatable member 100 that are in vicinity of the proximal opening 134 and the distal opening 122. Thus, for example, distal end 108 of inflatable member 100 can be removed (see, e.g., FIGS. 2B and 2C) along with portions of inflatable member 100 that are proximal to the proximal opening 134 of rigid tube member 112.

In another embodiment, instead of extending into and/or through the housing, a proximal open end of inflatable member 100 can be coupled to a distal end 144 of housing 136 in an substantially airtight fashion. Thus, everything inside housing 136 can be under the same pressure as inflatable member 100. As in the other embodiments, the housing 136 can have an interior space for receiving rigid tube member 112 inside housing 136; however, in this embodiment, when rigid tube member 112 is in housing 136, rigid tube member 112 does not substantially overlap with the proximal end of inflatable member 100. Instead, rigid tube member 112 is not inserted into inflatable member 100 until the collapsed portion 138 is inflated to form the expanded portion 142. Then, the rigid tube member 112 is expelled from housing 136 and directed into the proximal open end of inflatable member 100.

Various mechanisms can be provided for delivering rigid tube member 112 into the passageway defined by the expanded portion 142 of inflatable member 100. Such mechanisms can include both manually-operated mechanisms that provide direct tactile feedback to the surgeon and non-manual mechanisms that are motor-driven or otherwise powered. For example, an actuator 145 can be provided for moving rigid tube member 112 as described herein. Actuator 145 can comprise, for example, a lever or plunger that manually pushes the rigid tube member into the passageway defined by inflatable member 100. The lever or plunger can also be at least partially inside inflatable member 100 to facilitate the pushing of rigid tube member 112 through the inside of inflatable member 100. Alternatively, the lever or plunger can be positioned outside the inflatable member and can exert a force on the rigid tube member through inflatable member 100. FIGS. 3E and 3F show an actuator 145 that is a plunger-type mechanism that moves between a first non-deployed position (FIG. 3E) and a second deployed position (FIG. 3F) to move the rigid tube member 112 into the inflated collapsed portion 138.

As shown in FIGS. 3B-3F, a pressure gland 147 can be included on housing 136 to maintain pressure within housing 136 during deployment of actuator 145. In the embodiment shown in FIGS. 3B-3F, actuator 145 comprises a pushrod that is inserted through pressure gland 147 and into the proximal end of housing 136. Movement of the pushrod towards rigid tube member 112 causes a distal end of the pushrod to pierce the enlarged diameter portion 140 of inflatable member 100 and push the rigid tube member 112 downward into the inflated collapsed portion 138. Because inflatable member 100 is sealed to the hollow housing 136 at both ends (i.e., the proximal and distal end of housing 136), pressure can be maintained in the housing 136 as the push rod is inserted through pressure gland 147 and contacts rigid tube member 112.

In other embodiments, a motorized linear actuator can be provided to exert a force on rigid tube member 112 to cause it to move into the expanded portion 142 of inflatable member 100. In another embodiment, a magnet and a corresponding responsive material on or adjacent the rigid tube member 112 can be provided to push the rigid tube member 112 downward (e.g., distally) without requiring penetration and/or direct contact with inflatable member 100.

By delivering rigid tube member 112 through the inside of inflatable member 100 in the manners described herein, rigid tube member 112 does not directly contact the tissue surrounding inflatable member 100 during delivery of rigid tube member 112 from a position outside the body to a position at least partially inside of the body. Accordingly, the shear drag on the brain tissue caused by direct contact with rigid tube member 112 can be eliminated and/or greatly reduced in comparison to conventional methods that require directly contacting brain tissue during insertion of an endoscopic port. Moreover, the reduced diameter of the collapsed portion 142 only requires a very small channel for delivery of the inflatable member 100 through the cortex and white matter prior to dilatation of the inflatable member 100. In some embodiments, the diameter of the collapsed portion can be less than about 4 mm, less than about 3 mm, or even less than about 2 mm. Such reduced diameter delivery channels can facilitate deeper access while being less traumatic to the tissue surrounding the delivery channel than existing methods.

In some embodiments, rigid tube member 112 can be non-cylindrical. For example, rigid tube member 112 can be oval in cross section or shaped in another useful shape. Desirably, such shapes would not have sharp edges that could cause trauma to surrounding tissue. If desired, when used in combination with a non-cylindrical rigid tube member, inflatable member 100 can be also be non-cylindrical in cross section. For example, the inflatable member can be of the same general cross-sectional shape as the rigid tube member to facilitate delivery of the non-cylindrical rigid tube member.

In some embodiments, rather than delivering rigid tube member 112 through the lumen of expandable member 100 (i.e., within expandable member 100), rigid tube member 112 can be deployed down the outer edge of inflatable member 100 (i.e., so an inner surface of rigid tube member 112 is in contact with an outer surface of inflatable member 100). If rigid tube member 112 is delivered on the outside of inflatable member 100, inflatable member 100 can simply be withdrawn from within rigid tube member 112 to provide access through the passageway created by the expanded inflatable member 100 within the body. Thus, there is no need to cut portions of inflatable member 100 away to provide access to the proximal and/or distal openings of rigid tube member 112. A disadvantage of this approach, however, the shear forces on the tissue surrounding inflatable member are not as greatly reduced as in the case where rigid tube member 112 is delivered inside inflatable member 100 as described herein in other embodiments.

After lesion 104 is removed and/or other desired treatments are performed, rigid tube member 112 can be slowly withdrawn. In some embodiments, it may be desirable to further reduce the speed in which the brain tissue contracts back into passageway 114 that was maintained opened by rigid tube member 112. FIGS. 4A-4C and 5A-5C illustrate a method for further reducing the speed of contraction around passageway 114. As shown in FIG. 4B, a second inflatable member 150 can be inserted into rigid tube member 112 in the direction indicated by arrow 152. Second inflatable member 150 can be inflated so that an external diameter of second inflatable member 150 is slightly less than an inner diameter of rigid tube member 112, as shown in FIG. 4C.

After inflation of second inflatable member 150, rigid tube member 112 (and the portion of inflatable member 100 coupled therewith to form the double-walled tube) can be withdrawn with less immediate contraction of the brain tissue immediately surrounding rigid tube member 112. FIG. 5A illustrates the removal of rigid tube member 112 over second inflatable member 150 by pulling rigid tube member 112 in the direction indicated by arrow 154. After removal of rigid tube member 112, second inflatable member 150 can then be slowly deflated, allowing the brain tissue to slowly contract into the volume recently retracted by rigid tube member 112. When second inflatable member 150 is reduced in diameter to a desired size, such as the reduced diameter size that is shown in FIG. 5B, second inflatable member 150 can be completely withdrawn from the body as shown in FIG. 5C. After second inflatable member 150 is withdrawn from the body by pulling second inflatable member 150 in the direction indicated by arrow 156, the brain tissue can be allowed to continue to contract until it fills the void left by the withdrawal of second inflatable member 150.

By using the inflatable members disclosed herein, the speed of insertion, inflation, deflation, and removal can be more easily controlled by a surgeon. The systems and methods disclosed herein can be adapted to be formed in any desired size, including for example, sizes between 10 and 20 mm, thereby increasing versatility for visualization and resection purposes. Thus, the systems and methods disclosed herein can reduce trauma to healthy brain tissue, improve versatility of conduit size, and facilitate the control rate of brain tissue distortion during port introduction and/or port removal. This allows deeper and safer access for brain tumors in which surgery may not otherwise have been attempted.

Although the embodiments described herein are generally directed to the surgical removal of brain tumors, this technology has the potential to facilitate other surgical applications as well. For example, the dilatable ports disclosed herein can be used to deliver local therapies to deep-seated tumors and lesions (e.g. chemotherapeutic wafers, stem cells, etc.). In addition, the dilatable ports disclosed herein can be used for non-tumor surgery, such as the evacuation of intracerebral hemorrhages. Finally, the dilatable ports disclosed herein can be used in non-neurosurgical applications, such as laparoscopic surgery or thoracoscopic surgery, as a conduit through which surgical instruments could be introduced.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for providing an endoscopic port comprising:
    inserting a distal portion of an expandable member into soft tissue in a patient's body;
    inflating the distal portion of the expandable member to form a passageway in the soft tissue;
    delivering a rigid tube member into the passageway formed by the expandable member, the rigid tube member being delivered inside the inflated distal portion of the expandable member; and establishing a port between a proximal opening in the rigid tube member and a distal opening in the rigid tube member,
wherein establishing the port comprises cutting a distal end of the expandable member and removing the cut distal end from within the rigid tube member.

2. The method of claim 1, wherein the insertion of the distal portion of the expandable member comprises inserting a guide member into the distal portion and directing the guide member and distal portion of the expandable member through the soft tissue.

3. The method of claim 2, wherein the guide member is coupled to the distal end of the expandable member and the removal of the cut distal end comprises removing the guide member from within the rigid tube member.

4. The method of claim 1, wherein establishing the port further comprises cutting the expandable member around the proximal opening of the rigid tube member.

5. The method of claim 1, wherein the rigid tube member is positioned within a housing and the rigid tube member is delivered into the passageway by exerting a force on the rigid tube member to push it into the inflated distal portion of the expandable member.

6. The method of claim 5, wherein a proximal portion of the expandable member extends into the housing and the rigid tube member is positioned inside the proximal portion of the inflation member before being delivered into the passageway.

7. The method of claim 6, wherein the expandable member is entirely contained within a sealed volume of the inflation member before being delivered into the passageway.

8. The method of claim 5, wherein the exertion of the force on the rigid tube member to push it into the inflated distal portion of the expandable member is achieved by manually depressing a plunger, activating a motorized linear actuator, or magnetically coupling the rigid tube member with an external magnet.

9. The method of claim 1, further comprising:
inserting a second expandable member into the rigid tube member;
at least partially inflating the second expandable member within the endoscopic port;
removing the rigid tube member from the passageway; and
deflating the expandable member to reduce the speed at which the soft tissue surrounding the passageway expands to fill the passageway upon removal of the rigid tube member.

10. A method for providing an endoscopic port comprising:
inserting a distal portion of an expandable member into soft tissue in a patient's body;
inflating the distal portion of the expandable member to form a passageway in the soft tissue;
delivering a rigid tube member into the passageway formed by the expandable member, the rigid tube member being delivered along an outside surface of the inflated distal portion of the expandable member; and
removing the expandable member by withdrawing it through an inner passageway of the rigid tube to establish a port between a proximal opening in the rigid tube member and a distal opening in the rigid tube member.

11. A method for providing an endoscopic port comprising:
inserting a distal portion of an expandable member into soft tissue in a patient's body;
inflating the distal portion of the expandable member to form a passageway in the soft tissue;
delivering a rigid tube member into the passageway formed by the expandable member, the rigid tube member being delivered inside the inflated distal portion of the expandable member;
establishing a port between a proximal opening in the rigid tube member and a distal opening in the rigid tube member;
inserting a second expandable member into the rigid tube member;
at least partially inflating the second expandable member within the endoscopic port;
removing the rigid tube member from the passageway; and
deflating the expandable member to reduce the speed at which the soft tissue surrounding the passageway expands to fill the passageway upon removal of the rigid tube member.

* * * * *